United States Patent
Pol

(10) Patent No.: US 11,567,005 B2
(45) Date of Patent: Jan. 31, 2023

(54) METHOD IN A SURFACE PLASMON RESONANCE BIOSENSOR SYSTEM

(71) Applicant: CYTIVA SWEDEN AB, Uppsala (SE)

(72) Inventor: Ewa Pol, Uppsala (SE)

(73) Assignee: CYTIVA SWEDEN AB, Uppsala (SE)

( * ) Notice: Subject to any disclaimer, the term of this patent is extended or adjusted under 35 U.S.C. 154(b) by 205 days.

(21) Appl. No.: 15/767,838

(22) PCT Filed: Oct. 12, 2016

(86) PCT No.: PCT/EP2016/074516
§ 371 (c)(1),
(2) Date: Apr. 12, 2018

(87) PCT Pub. No.: WO2017/064147
PCT Pub. Date: Apr. 20, 2017

(65) Prior Publication Data
US 2018/0299377 A1 Oct. 18, 2018

(30) Foreign Application Priority Data
Oct. 12, 2015 (GB) .................................... 1517985

(51) Int. Cl.
*G01N 21/552* (2014.01)
*G01N 21/27* (2006.01)
*G01N 33/68* (2006.01)

(52) U.S. Cl.
CPC ......... *G01N 21/553* (2013.01); *G01N 21/274* (2013.01); *G01N 33/6803* (2013.01); *G01N 2201/127* (2013.01)

(58) Field of Classification Search
CPC .............. G01N 21/553; G01N 21/274; G01N 33/6803; G01N 2201/127
See application file for complete search history.

(56) References Cited

U.S. PATENT DOCUMENTS 10,151,694 B2 * 12/2018 Karlsson .............. G01N 21/553
2005/0197581 A1 9/2005 Ferguson et al.
(Continued)

FOREIGN PATENT DOCUMENTS

CN 101271066 A 9/2008
CN 101802598 A 8/2010
(Continued)

OTHER PUBLICATIONS

Davis—Determination of the Refractive Index Increments of SmallMolecules for Correction of Surface PlasmonResonance Data—Analytical Biochemistry—2000 (Year: 200).*

(Continued)

*Primary Examiner* — Benjamin R Whatley
*Assistant Examiner* — Jean Caraballo-Leon
(74) *Attorney, Agent, or Firm* — Jeff B. Vockrodt; Culhane Meadows, PLLC

(57) ABSTRACT

A method for determining instrument-dependent parameters of a surface plasmon resonance, SPR, biosensor system, and using those instrument-dependent parameters to measure the concentration of an analyte is provided herein. Also disclosed are methods of monitoring surface binding interactions of the analyte using the instrument-dependent parameters.

9 Claims, 1 Drawing Sheet

(56) References Cited

U.S. PATENT DOCUMENTS

| | | | |
|---|---|---|---|
| 2006/0040326 A1* | 2/2006 | Ohtsuka | G01N 21/553 435/7.1 |
| 2009/0030617 A1 | 1/2009 | Schell et al. | |
| 2010/0049444 A1* | 2/2010 | Likuski | G01N 33/721 702/19 |
| 2012/0208298 A1* | 8/2012 | Pol | G01N 33/54373 436/501 |
| 2013/0017624 A1* | 1/2013 | Karlsson | G01N 33/54373 436/501 |
| 2014/0141529 A1 | 5/2014 | Karlsson et al. | |
| 2014/0147937 A1 | 5/2014 | Karlsson et al. | |
| 2014/0156202 A1 | 6/2014 | Floridia et al. | |

FOREIGN PATENT DOCUMENTS

| | | |
|---|---|---|
| JP | 2006527365 A | 11/2006 |
| JP | 2007527529 A | 9/2007 |
| JP | 2013508720 A | 3/2013 |
| JP | 2014510923 A | 5/2014 |
| JP | 2014521063 A | 8/2014 |
| WO | 2004109284 A1 | 12/2004 |
| WO | 2015197500 A1 | 12/2015 |

OTHER PUBLICATIONS

Pol—Biosensor-based characterization of serum antibodies during development of an anti-IgE immunotherapeutic against allergy and asthma—Journal of Molecular Recognition—2007 (Year: 2007).*
Sigmundsson et al (Determination of Active Concentrations and Association and Dissociation Rate Constants of Interacting Biomolecules: An Analytical Solution to the Theory for Kinetic and Mass Transport Limitations in Biosensor Technology and its Experimental Verification, Biochemistry, 2002 (Year: 2002).*
International Search Report and Written Opinion for corresponding PCT application No. PCT/EP2016/074516 dated Dec. 12, 2016; 18 pages.
Feng Feng et al: "Bayesian Estimation of the Active Concentration and Affinity Constants Using Surface Plasmon Resonance Technology", PLOS ONE, vol. 10, No. 6, Jun. 22, 2015; pp. 4-14.
Ewa Pol: "The Importance of Correct Protein Concentration for Kinetics and Affinity Determination in Structure-function Analysis", Journal of Visualized Experiments, No. 37, Mar. 17, 2010; 7 pages.
Pol, Ewa et al: "Evaluation of Calibration-Free Concentration Analysis Provided by Biocore (TM) Systems" Analytical Biochemistry, Elsevier, Amsterdam, NL. vol. 510, Jul. 9, 2016; pp. 88-97.
Visentin, Jonathan et al: "Calibration Free Concenlalion Analysis by Surface Plasmon Resonance In a Capture Mode", Talanta, vol. 148, Nov. 10, 2015; pp. 480-483.
Robert Karlsson: "Biosensor Binding Data and its Applicability to the determination of Active Concentration", Biophysical Reviews, Oct. 17, 2016; 12 pages.
GB search report for corresponding application No. GB1517985.6 dated Sep. 16, 2016; 3 pages.
Chinese Office Action Received in Application No. 20168059486.3 dated Jun. 2, 2020, 21 pages. (with translation).
Feng, et al., "Bayesian Estimation of the Active Concentration and Affinity Constants Using Surface Plasmon Resonance Technology," PLOS One, Nov. 2, 2015, vol. 10, No. 6, 17 pages.
Japanese Office Action received in Application No. 2018-537726 dated Nov. 9, 2020, 8 pages.
Communication pursuant to Article 94(3) EPC, dated Mar. 4, 2022, 12 pages.

* cited by examiner

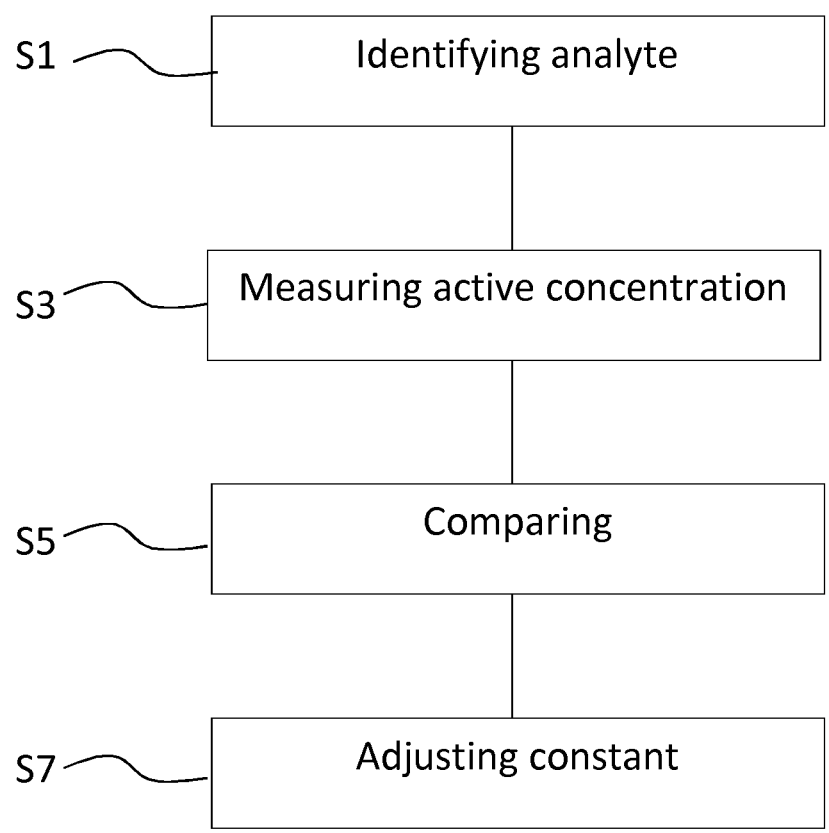

METHOD IN A SURFACE PLASMON RESONANCE BIOSENSOR SYSTEM

CROSS-REFERENCE TO RELATED APPLICATION

This application is a filing under 35 U.S.C. 371 of international application number PCT/EP2016/074516, filed Oct. 12, 2016, which claims priority to GB application number GB1517985.6, filed Oct. 12, 2015, the entire disclosure of each of which is hereby incorporated by reference.

TECHNICAL FIELD

The present invention relates to a method for determining instrument-dependent parameters of a surface plasmon resonance, SPR, biosensor system and to a method for monitoring surface binding interactions in an SPR biosensor.

BACKGROUND

Analytical sensor systems (i.e., label-free systems) that can monitor molecular interactions in real time are gaining increasing interest. These systems are often based on optical biosensors and usually referred to as interaction analysis sensors or biospecific interaction analysis sensors. A representative biosensor system is the Biacore™ instrumentation sold by GE Healthcare Life Sciences, which uses surface plasmon resonance (SPR) for detecting interactions between molecules in a sample and molecular structures immobilized on a sensing surface. With the Biacore™ systems it is possible to determine in real time without the use of labeling not only the presence and concentration of a particular molecule in a sample, but also additional interaction parameters such as, for instance, the association rate and dissociation rate constants for the molecular interaction. The apparatus and theoretical background are fully described in the literature (see e.g., Jonsson, U., et al., BioTechniques 11: 620-627 (1991)). Normally, the technique involves the immobilization of a ligand to the special optical sensor surface of a sensor chip (flow cell), contacting the sensor chip with a flow of sample containing the analyte of interest, and then measuring the change in the surface optical characteristics of the sensor chip arising from the binding between the ligand and the analyte. For further details on SPR, reference is also made to U.S. Pat. Nos. 5,313,264, 5,573,956 and 5,641,640.

Calibration-free concentration analysis (CFCA) calculates the analyte concentration from the measured mass transport properties and values for the diffusion coefficient and molecular weight, provided as evaluation variables when the assay is run. The evaluation is based on fitting the sensorgram data to a model of interaction kinetics that contains a mass transport component. The mass transport parameters are calculated from the supplied diffusion coefficient, flow cell characteristics and molecular weight. With the analyte concentration set as a globally fitted variable the unknown concentration of the analyte can be determined.

The measurements, including CFCA, performed by SPR-based biosensor systems uses a system dependent constant that is dependent on chip used, flow cell characteristics and other instrument characteristics, and allows to convert measured response units into mass units.

BRIEF DESCRIPTION

An object of the present invention is to improve the measuring accuracy of measurements performed in a surface plasmon resonance (SPR) biosensor system.

This is achieved in a method according to claim 1. Hereby the instrument dependent part of the constant used is adjusted for each specific instrument, flow system and sensor surface and more accurate measurements can be achieved.

Different embodiments are described in the dependent claims.

BRIEF DESCRIPTION OF THE DRAWINGS

FIG. 1 is a flow chart showing the method steps of one embodiment of the invention.

DETAILED DESCRIPTION

Calibration free concentration analysis, CFCA, can be described as the method that measures an active concentration, i.e. the concentration of molecules capable of binding to the target attached to sensor surface, by use of SPR-based biosensor systems.

The active concentration of a protein is defined through the interaction of the protein with its binding partner and can differ from the total protein concentration if some of the molecules are incapable of binding. If a protein has several different binding sites, active concentration can be established for each binding site. In the current Biacore™ evaluation software, active concentration is called calibration free concentration analysis (CFCA).

In a typical experiment, the interaction partner (ligand) is attached to the sensor surface and a molecule of interest (analyte), for which the concentration is measured, is delivered in a constant laminar flow in a well-defined flow cell. In this approach, only the concentration of analyte fraction that is capable of binding to the immobilized ligand is measured. The binding between the ligand and the analyte is a two-step process consisting of (i) the diffusion of analyte from bulk to the surface and (ii) the analyte-to-ligand binding. If the rate of diffusion is much slower than the rate of binding between the molecules, then the rate of complex formation is limited by the transport rate, and for the reversed case, the observed initial rate of complex formation corresponds to intrinsic reaction rate.

A mass transport coefficient, $k_m$, describes the flux of molecules with diffusion coefficient D, in the flow cell of height h, to the sensor surface as described by equation 1:

$$k_m = 0.98 \cdot \sqrt[3]{\frac{D^2 \cdot f}{1.5^{-3} \cdot h^2 \cdot w \cdot l}} \tag{1}$$

In practical SPR detection systems, the effective length differs from the flow cell length and $k_m$ is defined as:

$$k_m = 0.98 \cdot \sqrt[3]{\frac{D^2 \cdot f}{h^2 \cdot w \cdot (\alpha - \beta/2 + 1.5^{-3}\beta)}} \tag{2}$$

Where $\alpha$ is the distance from the flow cell inlet to the center of the detection area and $\beta$ is the detection area length.

The diffusion coefficient of the analyte that is required for calculation of the concentration, can be obtained experimentally or from the three dimensional structure, if available, using Hydropro program. An empirical formula (equation 3) based on Stoke's law and the Einstein-Sutherland equation can also be used to assess D, although relative frictional ratio, $f/f_0$ of the analyte, and viscosity of the solvent, .eta., must be known. For typical water-based buffers, the viscosity of water can be assumed.

$$D = \frac{324.3 \times 10^{-11}}{f/f_0 \times \eta/\eta_0 \times \sqrt[3]{MW}} \quad m^2/s \quad (3)$$

$\eta_0$ is the viscosity of the solvent at 20° C.

To relate the transport coefficient to the SPR biosensor system (in this example the Biacore™) response and to allow specific input of the actual flow rate, $t_c$ is introduced as a transport coefficient.

$$t_c = \text{Form Factor} \times f^{1/3} \times G \times MW \times k_m \quad (4)$$

By expressing G, the surface concentration with unit $g/m^2$, in RU, with 1 RU equal to $10^{-6}$ $g/m^2$, and by setting the Form Factor to 0.81, the relation to $k_m$ is established and $$t_c = 0.81 \times 10^9 \times f^{1/3} > MW \times k_m \quad (5)$$

G was initially calculated assuming a 100 nm dextran layer. However, the extension of the dextran layer may vary with immobilization level and varies between chip types. Therefore, some uncertainty in the calculation of G-factor exists and a user may need some flexibility to change it. The Form Factor allows this flexibility and the current value of 0.81 used in Biacore™ evaluation software has been determined empirically.

The degree of mass transport limitation, MTL, depends on the combination of several parameters including flow cell dimensions, flow rate, density of the free binding sites on the surface, kinetic constant of the interaction, and the diffusion coefficient. For a given analyte-ligand pair and flow cell, MTL is promoted by a high concentration of free, unoccupied ligand, which is expected to happen at high immobilization and low response levels. Moreover, under these conditions, the effect of complex, deviating from 1:1 interaction scheme, binding, can be neglected.

The degree of MTL can be estimated from initial binding rates observed under transport limited (eq. 6) and kinetic (eq. 7) conditions:

$$dR/dt = t_c \times C \text{ and} \quad (6)$$

$$dR/dt = k_a \times C \times R_{max} \quad (7)$$

The degree of transport limitation can be estimated from:

$$MTL = \frac{1}{1 + \frac{t_c}{k_a \times R_{max}}} \quad (8)$$

For the transport limited case $k_a \times R_{max} \gg t_c$ and MTL approaches

For the kinetic case $k_a \times R_{max} \ll k_t$ and MTL approaches 0

These relationships can be used to estimate the possibility of CFCA for a specific interaction but is also impractical as the association rate constant for the interaction has to be known and this is not always the case.

According to the invention a method for determining instrument-dependent parameters of a surface plasmon resonance, SPR, biosensor system is provided. FIG. 1 is a flow chart showing the method steps of one embodiment of the invention. The method comprises the steps:

S1: Identifying an appropriate analyte for use in a calibration step. Said analyte needs to have a known molecular weight, a known diffusion constant, a known refractive index increment and a known concentration. Said analyte also needs to bind to a chip used in the biosensor system. Either the analyte can bind to the chip itself or to a binding partner, a ligand, that is attached to the chip.

S3: Measuring active concentration by use of the SPR biosensor system according to a known method using the identified analyte and the chip. Said known method includes the use of an instrument-dependent constant that is not adapted for each specific instrument, chip and flow cell combination.

S5: Comparing the known concentration of the analyte with the active concentration measured in step S3.

S7: Adjusting the instrument-dependent constant used in the known method for measuring active concentration according to the difference retrieved in step S5.

In one embodiment of the invention the method further comprises a step of calculating constants that convert responses into mass units from the adjusted instrument-dependent constant retrieved in step S7.

In one embodiment of the invention the method further comprises a step of calculating other constants connected to flow cells, chips, and other instrument connected quantities from the adjusted instrument-dependent constant retrieved in step S7.

In one embodiment of the invention the step of identifying an appropriate analyte also includes that the analyte needs to have a known affinity and known kinetic constants to the binding partner. Furthermore, in one embodiment of the invention a mass transport constant is used in calculation algorithms used for the calculations described above.

In one embodiment of the invention step S3 comprises measuring active concentration by a method called calibration free concentration analysis, CFCA. Furthermore, in one embodiment of the invention the constants calculated that convert responses into mass units are a constant called G and a constant called Form Factor which both are used in calculating a transport coefficient needed for the calibration free concentration analysis.

Furthermore according to the invention a method for monitoring surface binding interactions in an SPR biosensor is provided. Said method comprises the steps of:

determining instrument-dependent parameters for the currently used specific instrument, chip and flow cell combination according to the steps S1-S7 described above;

using this new instrument-dependent constant retrieved in step S7 for determining SPR-related responses.

In one embodiment of the invention the new instrument-dependent constant retrieved in step S7 is used for determining concentration of the analyte.

A new, instrument/system/chip/-depending constant, retrieved in step S7, can also be used for other purposes, like to uniform signals retrieved from different systems.

Calibration free concentration analysis is used to determine concentration without standards. The method works in conditions of mass transport limitation existing in the flow cell and on the sensor surface.

The events in the flow cell and on the sensor surface can be described as follows:

The binding of a macromolecular particle, e.g., a protein in the bulk ($A_{bulk}$) to the molecule on the chip surface (B) is a two-step process. In the first step protein from the bulk is transported to the surface ($A_{surf}$) with mass transport coefficient $k_m$, and in the second step, the binding between $k_{surf}$ and B occurs with association constant $k_a$ and dissociation constant $k_d$ and complex AB is formed.

If the transport of $A_{bulk}$ to sensor surface is slower than binding of $A_{surf}$ to B, then the mass transport limitation occurs and active concentration can be measured.

$$A_{bulk} \underset{k_m}{\overset{k_m}{\rightleftharpoons}} A_{surf} + B$$

$$A_{bulk} \underset{k_m}{\overset{k_m}{\rightleftharpoons}} A_{surf} + B \underset{k_d}{\overset{k_a}{\rightleftharpoons}} AB$$

The experimental procedure includes monitoring of responses on at least two widely separated flow rates and evaluation with appropriate model.

The binding phases of the curves (i.e., sensorgrams) obtained from such an experiment are fitted to a bi-molecular interaction model with mass transfer term ($k_t$), in which active concentration (Conc) is a fitted parameter:

$A$(solution)=Conc $A[0]=0$ $dA/dt=kt*(\text{Conc-}A)-(ka*A*B-kd*AB)$ $B[0]=R\text{Max}$ $dB/dt=-(ka*A*B-kd*AB)$ $AB[0]=0$ $dAB/dt=(ka*A*B-kd*AB)$ Total response:

$AB+RI$

In this model, the value of the mass transport constant, $k_t$, is introduced as a constant, which is calculated according to a formula:

$$k_t = G \times Mw \times 0.98 \times \sqrt[3]{\frac{D^2 \times f}{0.3 \times h^2 \times w \times l}}$$

where G is the factor, Mw is the molecular weight, $D$ is the diffusion coefficient, $f$ is the flow rate, and $h$, $w$, $l$ are the height, width, and length of the flow cell.

If we group the parameters in this formula into protein-dependent and instrument-dependent, we obtain:

$$k_t = \underbrace{Mw \times \sqrt[3]{D^2}}_{\substack{\text{analyte-dependent} \\ \text{parameters} \\ \text{Const}_{analyte}}} \times \underbrace{G \times 0.98 \times \sqrt[3]{\frac{1}{(0.3 \times h^2 \times w \times l)}}}_{\substack{\text{instrument-dependent} \\ \text{parameters} \\ \text{Const}_{instr}}} \times \underbrace{\sqrt[3]{f}}_{\text{variable}}$$

Or:

$k_t = G \times \text{Const}_{analyte} \times \text{Const}_{instr} \times \sqrt[3]{f}$ For a proposed calibration of an SPR biosensor system, we would need:

A model system, fulfilling mass transport limited conditions, in which an analyte has well defined concentration and $\text{Const}_{analyte}$, i. e., molecular weight and diffusion coefficient.

In a calibration procedure, the experiment will be performed in the same manner as in CFCA, but the experimental data would be fitted to a bi-molecular interaction model with mass transfer term ($k_t$), in which Concentration (Conc) is a constant and $k_t$ is fitted. $\text{Const}_{instr}$ is then calculated from $$\text{Const}_{instr} = \frac{k_1}{\text{Const}_{analyte}} \times \frac{1}{\sqrt[3]{f}}$$

Alternatively, the concentration is fitted in same way as in CFCA and the calculated concentration is then compared with true, well-defined concentration of analyte. The difference is an "instrument error" and $\text{Const}_{instr}$ can be adjusted.

Candidates to model system that fulfills the requirements for a calibrant (i.e., mass transport limited conditions and well-defined concentration and $\text{Const}_{analyte}$) are, for example, certified vitamin standards (analytes with well-defined concentrations) with their interaction partners.

The invention claimed is:

1. A method for measuring the active concentration of an analyte having an unknown concentration using a surface plasmon resonance, SPR, biosensor system, the method comprising the steps of:
   a) measuring an active concentration of a known analyte using the SPR biosensor system according to a first method, the SPR biosensor including a chip to which the known analyte can bind, wherein said measuring an active concentration of the known analyte comprises determining the active concentration of the known analyte using an instrument-dependent constant of the SPR biosensor system, wherein the instrument dependent constant includes the width, the height and the length of a flow cell of the SPR biosensor and the known analyte has a known molecular weight, known diffusion constant, known refractive index increment and a known concentration at the time of measuring;
   b) comparing the known concentration of the known analyte with the active concentration measured in step a) to determine an instrument error
   c) adjusting the instrument-dependent constant of the SPR biosensor system used in the first method by the instrument error obtained in step b) to obtain an adjusted instrument-dependent constant of the SPR biosensor system; and
   d) measuring an active concentration of an analyte having an unknown concentration using the SPR biosensor with the adjusted instrument-dependent constant of the SPR biosensor system from step c).

2. The method according to claim 1, further comprising a step of calculating parameters used to convert SPR biosensor response into mass units from the adjusted instrument-dependent constant of the SPR biosensor system retrieved in step c).

3. The method according to claim 1, further comprising a step of calculating parameters of the flow cell, and/or parameters of a chip using the adjusted instrument-dependent constant of the SPR biosensor system retrieved in step c).

4. The method according to claim 1, wherein the first analyte has a known affinity parameter and a known kinetic parameter for a first binding partner.

5. The method according to claim 2, wherein a mass transport constant is used in the step of calculating said parameters.

6. The method according to claim 1, wherein step b) comprises measuring active concentration using a calibration-free concentration analysis.

7. The method of claim 1, wherein the method further comprises monitoring surface binding interactions of the second analyte in the SPR biosensor.

8. The method according to claim 1, wherein the first analyte is the same as the second analyte.

9. The method according to claim 1, wherein the measurement is conducted under mass transport limiting conditions.

* * * * *